United States Patent [19]

Klauke et al.

[11] Patent Number: 4,564,478
[45] Date of Patent: Jan. 14, 1986

[54] FLUORINATED THIOCARBONIC ACID ESTER-FLUORIDES

[75] Inventors: Erich Klauke, Odenthal; Engelbert Kühle, Bergisch-Gladbach, both of Fed. Rep. of Germany

[73] Assignee: Bayer Aktiengesellschaft, Leverkusen, Fed. Rep. of Germany

[21] Appl. No.: 670,693

[22] Filed: Nov. 13, 1984

[30] Foreign Application Priority Data

Nov. 17, 1983 [DE] Fed. Rep. of Germany ....... 3341516

[51] Int. Cl.$^4$ ............... C07C 153/017; C07C 153/023; C07C 148/00
[52] U.S. Cl. .................................. 260/455 R; 568/43; 549/30
[58] Field of Search ....................... 260/455 R; 568/43

[56] References Cited

U.S. PATENT DOCUMENTS 3,766,236 10/1973 Thaler et al. .................. 260/455 R

*Primary Examiner*—Henry R. Jiles
*Assistant Examiner*—Robert C. Whittenbaugh
*Attorney, Agent, or Firm*—Sprung Horn Kramer & Woods

[57] ABSTRACT

Novel fluorinated thiocarbonic acid ester-fluorides of the formula

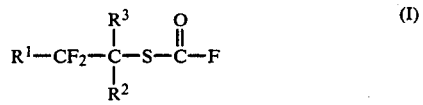

in which
$R^1$ represents alkyl, cycloalkyl or optionally substituted aryl and
$R^2$ and $R^3$ independently of one another represent hydrogen or alkyl, or
$R^1$ and $R^2$ together represent an alkylene chain, a new process for the preparation of the new compounds and their use as intermediates for the preparation of compounds having herbicidal properties.

Novel intermediates of the formulae

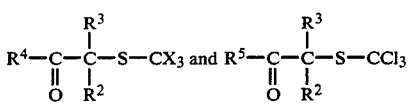

in which
$R^2$ and $R^3$ have the above-mentioned meaning,
$R^4$ is optionally substituted aryl,
$R^5$ is alkyl or cycloalkyl, and
X is fluorine or chlorine, at least one X representing chlorine.

12 Claims, No Drawings

FLUORINATED THIOCARBONIC ACID ESTER-FLUORIDES

The invention relates to new fluorinated thiocarbonic acid ester-fluorides, a new process for the preparation of these substances and their use as intermediates for the preparation of compounds having herbicidal properties.

Thiocarbonic acid ester-fluorides of the formula

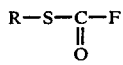

in which

R represents methyl, ethyl, n-propyl, iso-propyl, butyl, phenyl, p-chlorophenyl or p-fluorophenyl, have already been disclosed (compare J. Org. Chem. 30, 1317 (1965)). These compounds can be prepared either by reacting the mercaptans on which they are based with fluorocarbonyl chloride, or by treating the corresponding thiocarbonic acid ester-chlorides with anhydrous hydrofluoric acid. The disadvantage of these processes is that the particular starting substances required are difficult to obtain.

The present invention now provides, as new compounds, the fluorinated thiocarbonic acid ester-fluorides of the formula

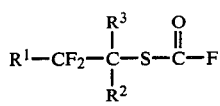

in which $R^1$ represents alkyl, cycloalkyl or optionally substituted aryl and $R^2$ and $R^3$ independently of one another represent hydrogen or alkyl, or $R^1$ and $R^2$ together represent an alkylene chain.

The resent invention further provides a new process for the preparation of fluorinated thiocarbonic acid ester-fluorides of the formula (I), which process comprises reacting a β-ketotrihalogenomethyl-thioether of the formula

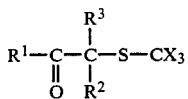

in which $R^1$, $R^2$ and $R^3$ have the abovementioned meaning and

X represents fluorine or chlorine, at least one X representing chlorine, with anhydrous hydrofluoric acid, if appropriate in the presence of a solvent.

Finally, the present invention provides the use of fluorinated thiocarbonic acid esterfluorides of the formula (I) as intermediates for the preparation of fluorinated thiolcarbamates, which have herbicidal properties.

Surprisingly, the fluorinated thiolcarbamates which can be prepared from the substances of the formula (I) according to the invention exhibit a better selective herbicidal activity than the compounds which are already known for the same intended use and are structurally the most similar. The course of the process according to the invention is also surprising. Thus, for example, it is known that fluorination of aliphatic or aromatic trichloromethyl-thioethers with hydrogen fluoride gives the corresponding compounds which are partly or completely fluorinated in the trichloromethyl group (compare Leibigs Ann. Chem. 621, 8 (1959), French Patent Specification No. 820,796 and Chemisches Zentralblatt 1938I, 1876). Analogously, it was to be assumed that the corresponding β-ketotrihalogenomethyl-thioethers fluorinated in the trihalogenomethyl group would be formed in the course of the reaction according to the invention by replacement of chlorine by fluorine. Against expectations, however, the substances of the formula (I) according to the invention are formed.

Formula (I) provides a general definition of the fluorinated thiocarbonic acid ester-fluorides according to the invention. In this formula, $R^1$ preferably represents straight-chain or branched alkyl with 1 to 12 carbon atoms, cycloalkyl with 3 to 8 carbon atoms or phenyl, which can be monosubstituted or polysubstituted by identical or different substituents from the group comprising halogen, alkyl with 1 to 4 carbon atoms, halogenoalkyl with 1 to 4 carbon atoms and 1 to 5 halogen atoms, alkoxy with 1 to 4 carbon atoms, halogenoalkoxy with 1 to 4 carbon atoms and 1 to 5 halogen atoms, alkylthio with 1 to 4 carbon atoms, halogenoalkylthio with 1 to 4 carbon atoms and 1 to 5 halogen atoms and/or nitro.

The radicals $R^2$ and $R^3$ independently of one another preferably represent hydrogen or straight-chain or branched alkyl with 1 to 4 carbon atoms.

Further, the radicals $R^1$ and $R^2$, together, preferably represent an alkylene chain with 3 to 5 carbon atoms. Particularly preferred compounds of the formula (I) are those in which $R^1$ represents straight-chain or branched alkyl with 1 to 8 carbon atoms, cycloalkyl with 3 to 7 carbon atoms or phenyl, which can be monosubstituted or polysubstituted by identical or different substituents from the group comprising fluorine, chlorine, halogenoalkyl with 1 or 2 carbon atoms and 1 to 3 fluorine or chlorine atoms, alkyl with 1 to 3 carbon atoms, halogenoalkyloxy with 1 or 2 carbon atoms and 1 to 3 carbon atoms and 1 to 3 fluorine or chlorine atoms, alkylthio with 1 to 3 carbon atoms, halogenoalkylthio with 1 or 2 carbon atoms and 1 to 3 fluorine or chlorine atoms and/or nitro, and radicals $R^2$ and $R^3$ independently of one another represent hydrogen or straight-chain or branched alkyl with 1 to 3 carbon atoms, or $R^1$ and $R^2$ together represent an alkylene chain with 3 or 4 carbon atoms. If acetonyl dichlorofluoromethyl thioether is used as the starting substance and anhydrous hydrofluoric acid is used as the fluorinating agent, the course of the process according to the invention can be illustrated by the following equation:

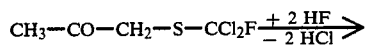

$$CH_3-CF_2-CH_2-S-COF$$

Formula (II) provides a general definition of the β-keto-trihalogenomethyl-thioethers required as starting substances in the process according to the invention. In this formula, $R^1$, $R^2$ and $R^3$ preferably have the meanings which have already been mentioned as preferred for these radicals in connection with the description of the substances of the formula (I) according to the invention. X represents fluorine or chlorine, but at least one X represents chlorine.

The substances listed in the two tables which follow may be mentioned as examples of β-keto-trihalogenomethylthioethers of the formula (II).

TABLE 1

$$R^1-\underset{\underset{O}{\|}}{C}-\underset{\underset{R^2}{|}}{\overset{\overset{R^3}{|}}{C}}-S-CCl_3 \quad (IIa)$$

| $R^1$ | $R^2$ | $R^3$ |
|---|---|---|
| $CH_3$ | $CH_3$ | $CH_3$ |
| $C_2H_5$ | $CH_3$ | H |
| $C_3H_7-n$ | $CH_3$ | H |
| $n-C_4H_9-$ | $CH_3$ | H |
| $n-C_5H_{11}$ | H | H |
| $n-C_6H_{12}$ | H | H |
| $n-C_{12}H_{25}$ | H | H |
| cyclopentyl | H | H |
| cyclohexyl | H | H |
| phenyl | H | H |
| 4-$H_3C$-phenyl | H | H |
| 3-$OCH_3$-phenyl | H | H |
| 4-$H_3CO$-phenyl | H | H |
| 2-F-phenyl | H | H |
| 3-F-phenyl | H | H |
| 4-F-phenyl | H | H |

TABLE 1-continued $$R^1-\underset{\underset{O}{\|}}{C}-\underset{\underset{R^2}{|}}{\overset{\overset{R^3}{|}}{C}}-S-CCl_3 \quad (IIa)$$

| $R^1$ | $R^2$ | $R^3$ |
|---|---|---|
| 3-Cl-phenyl | H | H |
| 2,4-di-$CH_3$-phenyl | H | H |
| 3,4-di-$CH_3$-phenyl | H | H |
| 4-$i$-$C_3H_7$-phenyl | H | H |
| 4-$CF_3O$-phenyl | H | H |
| 4-$CH_3S$-phenyl | H | H |
| 4-$CF_3S$-phenyl | H | H |

TABLE 2

$$R^1-\underset{\underset{O}{\|}}{C}-\underset{\underset{R^2}{|}}{\overset{\overset{R^3}{|}}{C}}-S-CCl_2F \quad (IIb)$$

| $R^1$ | $R^2$ | $R^3$ |
|---|---|---|
| $CH_3$ | $CH_3$ | $CH_3$ |
| $C_2H_5$ | $CH_3$ | H |
| $C_3H_7-n$ | $CH_3$ | H |
| $n-C_4H_9-$ | $CH_3$ | H |
| $n-C_5H_{11}$ | H | H |
| $n-C_6H_{12}$ | H | H |
| $n-C_{12}H_{25}$ | H | H |
| cyclopentyl | H | H |
| cyclohexyl | H | H |

TABLE 2-continued $$R^1-\underset{\underset{O}{\|}}{C}-\underset{\underset{R^2}{|}}{\overset{\overset{R^3}{|}}{C}}-S-CCl_2F \quad \text{(IIb)}$$

| $R^1$ | $R^2$ | $R^3$ |
|---|---|---|
| phenyl | H | H |
| 4-H$_3$C-phenyl | H | H |
| 3-OCH$_3$-phenyl | H | H |
| 4-H$_3$CO-phenyl | H | H |
| 2-F-phenyl | H | H |
| 3-F-phenyl | H | H |
| 4-F-phenyl | H | H |
| 3-Cl-phenyl | H | H |
| 3,4-(CH$_3$)$_2$-phenyl | H | H |
| 3,4-(H$_3$C)$_2$-phenyl | H | H |
| 4-i-C$_3$H$_7$-phenyl | H | H |
| 4-CF$_3$O-phenyl | H | H |
| 4-CH$_3$S-phenyl | H | H |
| 4-CF$_3$S-phenyl | H | H |
| 4-Cl-phenyl | H | H |
| 3-NO$_2$-phenyl | H | H |
| 3-CF$_3$-phenyl | H | H |

Some of the β-keto-trihalogenomethyl-thioethers of the formula (II) are known (compare U.S. Pat. No. 3,937,738 and E.Kühle "The Chemistry of the Sulfenic Acids", Georg Thieme Publ. Stuttgart, 1973, page 95).

The β-keto-trihalogenomethyl-thioethers of the formula

(IIc)

in which $R^2$, $R^3$ and X have the abovementioned meaning and $R^4$ represents optionally substituted aryl, have not hitherto been described. Thus, the present invention also provides, as new compounds, the β-keto-trihalogenomethyl-thioethers of the formula (IIc).

In the compounds of the formula (IIc), $R^4$ preferably represents phenyl, which can be monosubstituted or polysubstituted by identical or different substituents from the group comprising halogen, alkyl with 1 to 4 carbon atoms, halogenoalkyl with 1 to 4 carbon atoms and 1 to 5 halogen atoms, alkoxy with 1 to 4 carbon atoms, halogenoalkoxy with 1 to 4 carbon atoms and 1 to 5 halogen atoms, alkylthio with 1 to 4 carbon atoms, halogenoalkylthio with 1 to 4 carbon atoms and 1 to 5 halogen atoms and/or nitro.

Particularly preferred compounds of the formula (IIc) are those in which $R^4$ represents phenyl, which can be monosubstituted or polysubstituted by identical or different substituents from the group comprising fluorine, chlorine, alkyl with 1 to 3 carbon atoms, halogenoalkyl with 1 or 2 carbon atoms and 1 to 3 fluorine or chlorine atoms, alkoxy with 1 to 3 carbon atoms, halogenoalkoxy with 1 or 2 carbon atoms and 1 to 3 fluorine or chlorine atoms, alkylthio with 1 to 3 carbon atoms, halogenoalkylthio with 1 or 2 carbon atoms and 1 to 4 fluorine or chlorine atoms and/or nitro. The radicals $R^2$, $R^3$ and X preferably have those meanings which have already been mentioned above as preferred or as particularly preferred.

The compounds of the formula (IIc) can be prepared by a process in which ketones of the formula

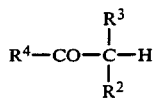 (III)

in which $R^2$, $R^3$ and $R^4$ have the abovementioned meaning, are reacted with trihalogenomethyl-sulphenyl chlorides of the formula $$Cl—S—CX_3 \quad (IV)$$

in which

X has the abovementioned meaning, if appropriate in the presence of a diluent, such as, for example, chloroform, at temperatures between 0° C. and 100° C. Working up is effected by customary methods.

The β-keto-trihalogenomethyl-thioethers of the formula

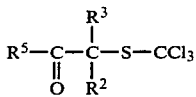 (IId)

in which $R^2$ and $R^3$ have the abovementioned meaning and $R^5$ represents alkyl or cycloalkyl, are also new. Thus, the present invention also also provides, as new compounds, the β-keto-trihalogenomethyl-thioethers of the formula (IId).

In the compounds of the formula (IId), $R^5$ preferably represents straight-chain or branched alkyl with 1 to 12 carbon atoms or cycloalkyl with 3 to 8 carbon atoms. Particularly preferred compounds of the formula (IId) are those in which $R^5$ represents straight-chain or branched alkyl with 1 to 8 carbon atoms or cycloalkyl with 3 to 7 carbon atoms. $R^2$ and $R^3$ preferably have those meanings which have already been mentioned above as preferred or as particularly preferred.

The compounds of the formula (IId) can be prepared by a process in which ketones of the formula

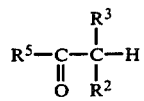 (V)

in which $R^2$, $R^3$ and $R^5$ have the abovementioned meaning, are reacted with trichloromethyl-sulphenyl chloride of the formula $$Cl—S—CCl_3 \quad (IVa)$$

if appropriate in the presence of an inert diluent, at temperatures between 0° C. and 100° C. Working up is effected by customary methods.

Anhydrous hydrofluoric acid is used as the fluorinating agent in the process according to the invention.

If appropriate, the reaction according to the invention can be carried out in the presence of a diluent which is inert under the reaction conditions. Solvents which can preferably be used here are chlorinated hydrocarbons, such as methylene chloride, chloroform and chlorobenzene.

The reaction temperature can be varied within a certain range in carrying out the process according to the invention. In general, the reaction is carried out at temperatures between −20° C. and +100° C., preferably between −10° C. and +70° C.

The reaction according to the invention can be carried out either under normal pressure or under increased pressure. The increased pressure can be up to 6 bar.

The reaction according to the invention is carried out in apparatuses which are usually customary for reactions for the replacement of chlorine by fluorine.

In carrying out the process according to the invention, a procedure is in general followed in which the anhydrous hydrofluoric acid is taken and the β-keto-trihalogenomethyl-thioether of the formula (II) is added at a low temperature. The use of an additional solvent is thereby in general dispensed with. However, if crystalline starting substances are to be added, this is advantageously effected by adding the substances in question dissolved in a solvent which is inert under the reaction conditions. The reaction according to the invention in general proceeds quite swiftly even at low temperatures; in most cases, it has already ended within a few hours under atmospheric pressure conditions. If starting materials which are relatively slow to react are used, the reaction is advantageously carried out under increased pressure at somewhat higher temperatures. It should be ensured here that the hydrogen chloride liberated can be let down via an adjustable valve.

The amount of hydrofluoric acid to be used depends on the number of chlorine atoms to be replaced. If 1 mole of β-ketotrihalogenomethyl-thioether of the formula (II) is used, at least 1 mole of anhydrous hydrofluoric acid must be employed per chlorine atom to be replaced. However, an excess is advantageously used, so that the hydrofluoric acid can simultaneously function as the solvent. In general, if 1 mole of β-keto-trihalogenomethyl-thioether of the formula (II) is used, 10 to 20 moles of hydrofluoric acid are employed per chlorine atom to be replaced. However, a larger excess does not impede the reaction.

The reaction mixture obtained after the fluorination is worked up by customary methods. In general, the reaction products are isolated by distillation. However, it is also possible first to extract the reaction mixture with a solvent which has only a low miscibility with hydrofluoric acid. Examples of such solvents are methylene chloride, chloroform, carbon tetrachloride, benzine, benzene and chlorobenzene.

The organic phase obtained after extraction is evaporated, if appropriate after prior washing and drying, and, if appropriate, the residue is distilled.

The fluorinated thiocarbonic acid ester-fluorides according to the invention can be used for the preparation of herbicidally active fluorinated thiolcarbamates of the formula

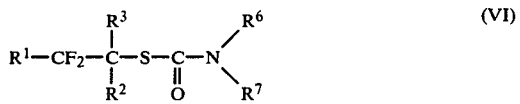

in which

R$^1$, R$^2$ and R$^3$ have the abovementioned meaning and

R$^6$ and R$^7$ independently of one another represent hydrogen, alkyl, alkenyl or alkinyl, or R$^6$ and R$^7$, together with the adjacent nitrogen atom, represent a saturated or unsaturated heterocyclic ring with 5 to 7 ring members.

The fluorinated thiolcarbamates of the formula (VI) are prepared here by a procedure in which fluorinated thiocarbonic acid ester-fluorides of the formula

in which

R$^1$, R$^2$ and R$^3$ have the abovementioned meaning, are reacted with compounds of the formula

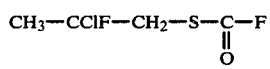

in which

R$^6$ and R$^7$ have the abovementioned meaning, if appropriate in the presence of a diluent and if appropriate in the presence of an acid-binding agent, at temperatures between 0° C. and 100° C.

The fluorinated thiolcarbamates of the formula (VI) have very good herbicidal properties, in particular selective herbicidal properties. They are particularly suitable for use for selectively combating Cyperaceae.

The preparation of the fluorinated thiocarbonic acid ester-fluorides of the formula (I) according to the invention and their use as intermediates for the synthesis of fluorinated thiolcarbamates of the formula (VI) can be seen from the following examples.

EXAMPLE 1

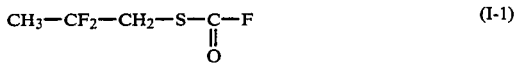

200 ml of anhydrous hydrofluoric acid were initially introduced into a reaction vessel of stainless steel. 200 g (1.05 moles) of acetonyl dichlorofluoromethylthioether were added dropwise in the course of 30 minutes at a temperature of −10° C., with stirring, evolution of hydrogen chloride starting immediately. The reaction mixture was warmed to 0° C. and was stirred at this temperature until virtually no further evolution of gas was observed. For subsequent working up, the reaction mixture was subjected to fractional distillation. 109 g (66% of theory) of 2,2-difluoropropanethiolcarbonic acid ester-fluoride were obtained in this manner.

Boiling point 103° C./100 mbar
n$_D^{20}$=1.3907

It was possible to isolate 2-fluoro-2-chloropropanethiolcarbonic acid ester-fluoride of the formula

from the last runnings by fine distillation.

Boiling point 74°–75° C./100 mbar
n$_D^{20}$=1.4320.

The substances listed by way of their formulae in Table 3 which follows were also prepared by the method described in Example 1.

TABLE 3

$$R^1-CF_2-\underset{\underset{R^2}{|}}{\overset{\overset{R^3}{|}}{C}}-S-\overset{\overset{O}{\|}}{C}-F \quad (I)$$

| Example No. | R$^1$ | R$^2$ | R$^3$ | Boiling point/ refractive index |
|---|---|---|---|---|
| 2 | CH$_3$— | CH$_3$— | H | 59° C./100 mbar<br>n$_D^{20}$ = 1.3950 |
| 3 | CH$_3$— | C$_2$H$_5$— | H | 76° C./100 mbar<br>n$_D^{20}$ = 1.4042 |
| 4 | CH$_3$—C(CH$_3$)(CH$_3$)— | H | H | 66° C./20 mbar<br>n$_D^{20}$ = 1.4160 |
| 5 | n-C$_3$H$_7$—n | C$_2$H$_5$— | H | 75° C./19 mbar<br>n$_D^{20}$ = 1.4148 |
| 6 | CH$_3$— | CH$_3$— | CH$_3$— | 72° C./50 mbar<br>n$_D^{20}$ = 1.4128 |
| 7 | —(CH$_2$)$_3$— | | H | 55–57° C./16 mbar |

EXAMPLE 8

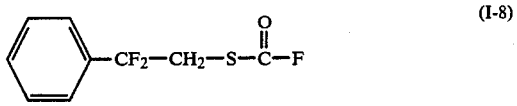

300 ml of anhydrous hydrofluoric acid were initially introduced into a reaction vessel of stainless steel. 530 g (2.09 moles) of fluorodichloromethyl-mercaptomethyl phenyl ketone were added dropwise in the course of one hour at a temperature of −8° C., with stirring. The evolution of hydrogen chloride which then started subsided after about one hour and was ended completely by subsequently stirring the mixture at room temperature for four hours. For subsequent working up, the reaction mixture was subjected to fractional distillation under reduced pressure. 342 g (74% of theory) of β-phenyl-β,β-difluoroethanethiol-carbonic acid ester-fluoride were obtained in this manner.

Boiling point=106° C./17 mbar
$n_D^{20} = 1.4891$

Preparation of the starting substance of the formula

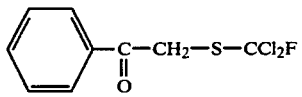 (II-1)

240 g (2 moles) of acetophenone were dissolved in 300 ml of chloroform and, after addition of 3 ml of ethanol and 109 g (0.64 mole) of fluorodichloromethanesulphenyl chloride, the mixture was heated to the reflux temperature. A further 400 g (2.36 moles) of fluorodichloromethane-sulphenyl chloride were added dropwise in the course of 30 minutes and the mixture was then heated under reflux for 5 hours. For subsequent working up, the reaction mixture was subjected to fractional distillation under reduced pressure. After first runnings of unchanged starting material, 126 g of fluorodichloromethyl-mercaptomethyl phenyl ketone were obtained in the form of a liquid of boiling point 128° C./0.4 mbar.

Refractive index: $n_D^{20} = 1.5653$

The yield is calculated as 87%, based on the acetophenone reacted.

The reaction product can also be employed for the fluorination with hydrofluoric acid without additional purification, after removal of the unchanged acetophenone.

EXAMPLE 9

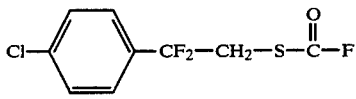 (I-9)

300 ml of anhydrous hydrofluoric acid were initially introduced into a reaction vessel of stainless steel. 370 g (1.29 moles) of 4-chlorophenyl fluorodichloromethyl-mercaptomethyl ketone were added dropwise in the course of one hour at a temperature of −8° C., with stirring. After the evolution of hydrogen chloride, which initially starts very swiftly, had subsided, the temperature of the reaction mixture was allowed to rise slowly to room temperature and the mixture was stirred until the evolution of hydrogen chloride had ended. For subsequent working up, the reaction mixture was subjected to fractional distillation under reduced pressure. 211 g (64.1% of theory) of β-(4-chloro-phenyl)-β,β-difluoromethanethiol-carbonic acid ester-fluoride were obtained in this manner in the form of a liquid.

Boiling point=126° C./16 mbar
$n_D^{20} = 1.5083$ 32 g of β-(4-chloro-phenyl)-β,β-difluoroethanethiol-carbonic acid ester-chloride of the formula

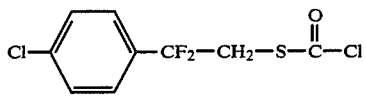

were also isolated from the last running.

Boiling point=145°-146° C./12 mbar
Melting point=45° C.

EXAMPLE 10

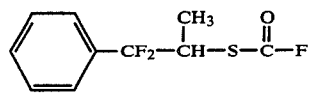 (I-10)

(2-Phenyl-2,2-difluoro-1-methyl)-ethane-thiolcarbonic acid ester-fluoride was also prepared by the method described in Examples 8 and 9.

Boiling point=107° C./14 mbar
$n_D^{20} = 1.4839$

EXAMPLE 11

Synthesis of the starting substance of the formula

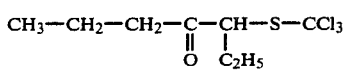 (II-2)

A mixture of 171 g (1.5 moles) of di-n-propyl ketone and 186 g (1 mole) of perchloromethylmercaptan was heated at 100° C. for 14 hours. Weak but regular evolution of hydrogen chloride was observed during the heating. For subsequent working up, the reaction mixture was subjected to fractional distillation under reduced pressure. 80 g of a product which essentially consisted of the β-keto-trichloromethylthioether of the formula (II-2) but was still contaminated by the substance of the formula

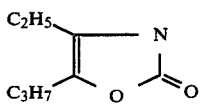

were obtained in this manner.

Boiling point=109° C./0.1 mbar
$n_D^{20} = 1.5156$

The compound described in Example 5 is formed from the substance mixture described above on reaction with hydrofluoric acid.

EXAMPLE 12

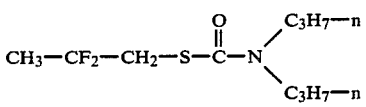 (VI-1)

A total of 20.2 g (0.2 mole) of di-n-propylamine was added dropwise to a solution of 15.8 g (0.1 mole) of 2,2-difluoropropanethiol-carbonic acid ester-fluoride in 100 ml of toluene at 20°-28° C., with stirring and cooling. The reaction mixture was stirred at room temperature for a further 30 minutes and then washed with water. After the organic phase had been dried over sodium sulphate, the solvent was stripped off under reduced pressure and the residue which remained was subjected to fractional vacuum distillation. 21 g (83% of theory) of N,N-di-n-propyl(2,2-difluoropropyl)-thiolcarbamic acid ester were obtained in this manner in the form of a liquid of boiling point 125° C./12 mbar The substances listed by way of their formulae in Table 4 which follows were also prepared by the method described in Example 12.

TABLE 4

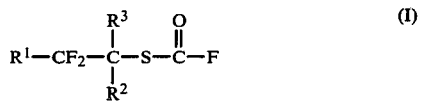

| Example No. | R¹ | R² | R³ | R⁶ | R⁷ | Physical constants |
|---|---|---|---|---|---|---|
| 13 | CH₃ | H | H | CH₃ | H | Boiling point 113° C./ 12 mbar |
| 14 | CH₃ | CH₃ | H | C₂H₅ | C₂H₅ | Boiling point 113–115° C./ 18 mbar |
| 15 | n-C₃H₇ | C₂H₅ | H | —(CH₂)₄— | | $n_D^{20} = 1.4808$ |
| 16 | C₆H₅ | C₂H₅ | H | —(CH₂)₄— | | $n_D^{20} = 1.5414$ |
| 17 | CH₃— | CH₃ | H | —(CH₂)₄— | | Boiling point 142–144° C./ 18 mbar |

The very good herbicidal activity of the fluorinated thiolcarbamates of the formula (VI) is illustrated by the following use example.

In this use example, the compound shown below was used as a comparison substance:

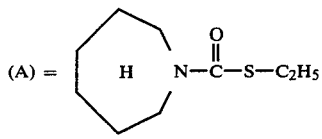

Ethyl hexahydro-1-H-azepine-1-thiolcarbamate (known from U.S. Pat. No. 3,198,786).

EXAMPLE A

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, the compound according to Example 17 exhibited a clearly better selective herbicidal activity than comparison substance (A) in combating Cyperus and Setaria in maize or cotton.

It will be understood that the specification and examples are illustrative but not limitative of the present invention and that other embodiments within the spirit and scope of the invention will suggest themselves to those skilled in the art.

What is claimed is:

1. A fluorinated thiocarbonic acid ester-fluoride of the formula $$R^1-CF_2-\underset{\underset{R^2}{|}}{\overset{\overset{R^3}{|}}{C}}-S-\overset{\overset{O}{\|}}{C}-F \quad (I)$$

in which

R¹ represents straight-chain or branched alkyl with 1 to 12 carbon atoms, cycloalkyl with 3 to 8 carbon atoms, or phenyl or phenyl substituted with substituents selected from the group consisting of halogen, alkyl with 1 to 4 carbon atoms, halogenoalkyl with 1 to 4 carbon atoms and 1 to 5 halogen atoms, alkoxy with 1 to 4 carbon atoms, halogenoalkoxy with 1 to 4 carbon atoms and 1 to 5 halogen atoms, alkylthio with 1 to 4 carbon atoms, halogenoalkylthio with 1 to 4 carbon atoms and 1 to 5 halogen atoms and nitro, and R² and R³ independently of one another represent hydrogen or straight-chain or branched alkyl with 1 to 4 carbon atoms, or R¹ and R² together represent an alkylene chain with 3 to 5 carbon atoms.

2. A fluorinated thiocarbonic acid ester-fluoride as claimed in claim 1, wherein R¹ is straight-chain or branched alkyl with 1 to 8 carbon atoms, cycloalkyl with 3 to 7 carbon atoms or phenyl, which can be monosubstituted or polysubstituted by identical or different substituents from the group comprising fluorine, chlorine, halogenoalkyl with 1 or 2 carbon atoms and 1 to 3 fluorine or chlorine atoms, alkyl with 1 to 3 carbon atoms, halogenoalkyloxy with 1 or 2 carbon atoms and 1 to 3 carbon atoms and 1 to 3 fluorine or chlorine atoms, alkylthio with 1 to 3 carbon atoms, halogenoalkylthio with 1 or 2 carbon atoms and 1 to 3 fluorine or chlorine atoms and/or nitro, and radicals R² and R³ independently of one another represent hydrogen or straight-chain or branched alkyl with 1 to 3 carbon atoms, or R¹ and R² together represent an alkylene chain with 3 or 4 carbon atoms.

3. A fluorinated thiocarbonic acid ester-fluoride as claimed in claim 1, characterized by the formula

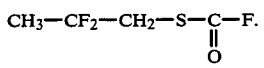

4. A fluorinated thiocarbonic acid ester-fluoride as claimed in claim 1, characterized by the formula

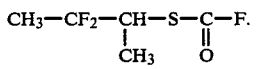

5. A fluorinated thiocarbonic acid ester-fluoride as claimed in claim 1, characterized by the formula

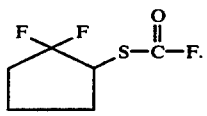

6. A process for the preparation of a fluorinated thiocarbonic acid ester-fluoride of the formula

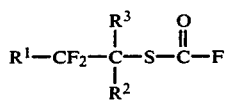

wherein
$R^1$ is alkyl, cycloalkyl or optionally substituted aryl,
$R^2$ and $R^3$ independently of one another are hydrogen or alkyl, or
$R^1$ and $R^2$ together represent an alkylene chain,
which process comprises reacting a β-keto-trihalogenomethyl-thioether of the formula

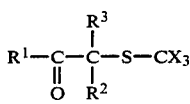

in which
$R^1$, $R^2$ and $R^3$ have the abovementioned meaning and
X represents fluorine or chlorine, at least one X representing chlorine, with anhydrous hydrofluoric acid.

7. A process as claimed in claim 6, wherein the reaction is effected in the presence of a diluent.

8. A process as claimed in claim 6, wherein the reaction is effected at a temperature of from −20° C. to +100° C.

9. A β-keto-trihalogenomethylthio-ether of the formula

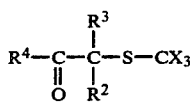

in which
$R^2$ and $R^3$ independently of one another represent hydrogen or straight-chain or branched alkyl with 1 to 4 carbon atoms,
$R^4$ represents phenyl or phenyl substituted with substituents selected from the group consisting of halogen, alkyl with 1 to 4 carbon atoms, halogenoalkyl with 1 to 4 carbon atoms and 1 to 5 halogen atoms, alkoxy with 1 to 4 carbon atoms, halogenoalkoxy with 1 to 4 carbon atoms and 1 to 5 halogen atoms, alkylthio with 1 to 4 carbon atoms, halogenalkylthio with 1 to 4 carbon atoms and 1 to 5 halogen atoms, and nitro and
X represents fluorine or chlorine, at least one X representing chlorine.

10. A β-keto-trihalogenomethylthio-ether of the formula

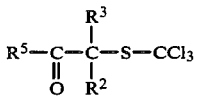

in which
$R^2$ and $R^3$ independently of one another represent hydrogen or straight-chain or branched alkyl having 1 to 4 carbon atoms and
$R^5$ represents straight-chain or branched alkyl with 1 to 12 carbon atoms or cycloalkyl having 3 to 8 carbon atoms.

11. A beta-keto-trihalogenomethyl-thio-ether according to claim 10, wherein for $R^5$ said alkyl has 1 to 8 carbon atoms.

12. A beta-keto-trihalogenomethyl-thio-ether according to claim 10, wherein for $R^5$ said cycloalkyl has 3 to 7 carbon atoms.

* * * * *